United States Patent
Sakai et al.

[11] Patent Number: 5,965,488
[45] Date of Patent: Oct. 12, 1999

[54] PLANT GROWTH REGULATING COMPOSITION COMPRISING EPOXYCYCLOHEXANE DERIVATIVES AND BRASSINOSTEROIDS AS WELL AS METHOD OF REGULATING PLANT GROWTH COMPRISING THE APPLICATION THEREOF

[75] Inventors: Kunikazu Sakai, Tokyo; Yasuo Kamuro, Aichi; Suguru Takatsuto, Niigata; Tsuyoshi Watanabe; Hiroki Kuriyama, both of Kanagawa, all of Japan

[73] Assignees: Sagami Chemical Research Center, Kanagawa; Tama Biochemical Co. Ltd., Tokyo; Bal Planning Co., Ltd., Ichihomiya, all of Japan

[21] Appl. No.: 09/066,805

[22] Filed: Apr. 24, 1998

Related U.S. Application Data

[60] Division of application No. 08/809,051, Mar. 13, 1997, Pat. No. 5,801,123, which is a continuation-in-part of application No. PCT/JP95/01816, Sep. 13, 1995.

[30] Foreign Application Priority Data

Sep. 14, 1994 [JP] Japan ................. 6-244863
Sep. 14, 1994 [JP] Japan ................. 6-244937

[51] Int. Cl.[6] ............................. A01N 43/20; A01N 43/22
[52] U.S. Cl. ............................. 504/140; 504/291
[58] Field of Search ....................... 504/140, 291

[56] References Cited

U.S. PATENT DOCUMENTS 5,254,694 10/1993 Sakai et al. ............... 549/546

OTHER PUBLICATIONS

Sakai et al., Tetrahedron (1992), 48 (38), 8229–38.
Gmuender et al., Helv. Chim. Acta (1990) 73(7), 1954–69.
Buschor et al., Helv. Chim. Acta (1990) 73(4), 1002–21.
Acemoglu et al., Helv. Chim. Acta (1988) 71(5), 931–56.
Nagano et al., Agric. Biol. Chem., (1980) 44(9), 2095–8.
Nanzyo et al., Agric. Biol. Chem., (1977), 41(9), 1711–20.

Primary Examiner—S. Mark Clardy
Attorney, Agent, or Firm—Fish & Richardson P.C.

[57] ABSTRACT

The present invention relates to a plant growth regulator comprising as an active ingredient an epoxycyclohexane derivative represented by general formula (1):

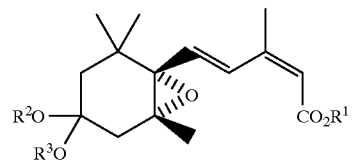

(1)

wherein $R^1$ is a hydrogen atom, a $C_1$–$C_6$ alkyl group or $C_3$–$C_6$ cycloalkyl group, and $R^2$ and $R^3$ are independently $C_1$–$C_6$ alkyl groups or are combined to form a $C_2$–$C_3$ polymethylene group which may be substituted with a $C_1$–$C_6$ alkyl group, as well as to a plant growth regulator comprising the epoxycyclohexane derivative and a brassinosteroid as active ingredients. The epoxycyclohexane derivatives exhibit a potent plant growth regulating action which is equivalent to or higher than that of abscisic acid, and are useful as plant growth regulators such as a plant growth accelerator, a germination growth accelerator, a transpiration and wilting inhibitor, a cold resistance enhancer, an accelerator for growing, thickening or maturing fruits, roots, stems or bulbs, etc. A synergistic effect is achieved by combination of the epoxycyclohexane derivative with a brassinosteroid.

12 Claims, No Drawings

PLANT GROWTH REGULATING COMPOSITION COMPRISING EPOXYCYCLOHEXANE DERIVATIVES AND BRASSINOSTEROIDS AS WELL AS METHOD OF REGULATING PLANT GROWTH COMPRISING THE APPLICATION THEREOF

This is a divisional of U.S. application Ser. No. 08/809,051, filed Mar. 13, 1997, now U.S. Pat. No. 5,801,123, which is a 371 of PCT/JP95/01816, filed Sep. 13, 1995, which claims priority under 119 of Japan Patent Application Nos. 244863/1994, filed Sep. 14, 1994 and 244937/1994, filed Sep. 14, 1994.

TECHNICAL FIELD

The present invention relates to novel epoxycyclohexane derivatives and a plant growth regulator with abscisic acid-like physiological actions.

BACKGROUND ART

Abscisic acid is one of plant hormones such as auxin, gibberellin, cytokinin, ethylene etc. Since abscisic acid was found in 1963, its physiological actions including abscission layer formation, dormancy induction, germination suppression, flowering suppression, bolting (flower stalk development) suppression, transpiration suppression, aging promotion, and stress resistance (e.g. cold resistance enforcement) came to be known. Although it is assumed that abscisic acid generally exhibits a growth suppressing action as described above, it was recently found that similar to other plant hormones, abscisic acid exhibits both promoting and suppressing effects depending on its concentration, and for example it promotes plant growth to raise the yield at low concentration (Nakabori et al., Bulletin of the Aomori Agricultural Experiment Station in 1991 (1992)). Further application to the promotion of thickening and maturing fruits (Japanese Patent LOP Publication Nos. 264,005/1992, 264,006/1992 and 264,007/1992), prevention of flowers or unmatured fruits from falling (Japanese Patent LOP Publication No. 139,911/1993), growth promotion for agricultural products (Japanese Patent LOP Publication No. 178,705/1993) or flowering promotion (Japanese Patent LOP Publication No. 186,303/1993) is known.

However, abscisic acid is expensive and among optical isomers of abscisic acid, natural type one demonstrates higher effects, and thus abscisic acid is not practically used. Recently, a method of producing natural type abscisic acid by culturing a microorganism of the genus Botrytis was developed, but it is hard to say that this method is satisfactory (Japanese Patent LOP Publication Nos. 296,696/1988, 296,697/1988 and 60,590/1990). Some reports have been made of its organic synthesis, but there remain problems with a large number of steps, costs, stereoselectivity (*Helv. Chim. Acta,* 71, 931 (1988); *J. Org. Chem.,* 54, 681 (1989); and Japanese Patent LOP Publication No. 184,966/1991).

Out of those compounds which relate to the plant growth regulator of the present invention, a free carboxylic acid and methyl ester derivative are described in the above literatures as intermediates for chemically synthesizing abscisic acid, but it is not disclosed that such intermediates exhibit abscisic acid-like physiological actions.

On one hand, brassinosteroids are a group of ubiquitous compounds present in plants, and exhibit specific physiological growth actions, such as growth promotion, fertilization and fructification promotion, cold resistance enforcement, promotion for thickening fruits etc., and promotion for germinating or rooting of seeds or cuttings.

However, it was not known that an intimate mixture of abscisic acid or an abscisic acid-like substance and a brassinosteroid exhibits a synergistic effect on plant growth regulation.

DISCLOSURE OF THE INVENTION

The object of the present invention is to provide a novel and highly active substance showing abscisic acid-like physiological actions and a highly active plant growth regulator.

As a result of their eager research, the present inventors found that a specific epoxycyclohexane derivative shows excellent abscisic acid-like physiological actions and further that an intimate mixture of said compound and a brassinosteroid acts synergistically on plants to exhibit a strong regulatory action on their growth, to complete the present invention.

That is, the present first invention relates to a plant growth regulator comprising as an active ingredient an epoxycyclohexane derivative represented by general formula (1):

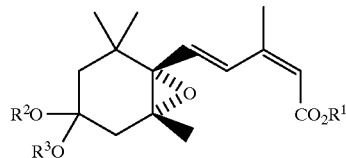

(1)

wherein $R^1$ is a hydrogen atom, $C_1$–$C_6$ alkyl group or $C_3$–$C_6$ cycloalkyl group, and $R^2$ and $R^3$ are independently $C_1$–$C_6$ alkyl groups or are combined to form a $C_2$–$C_3$ polymethylene group which may be substituted with a $C_1$–$C_6$ alkyl group, and in particular to a plant growth accelerator, a germination growth accelerator, a transpiration and wilting inhibitor, a cold resistance enhancer, and an accelerator for growing, thickening or maturing fruits, roots, stems or bulbs.

The present second invention relates to a plant growth regulator comprising as active ingredients an epoxycyclohexane derivative represented by general formula (1) and a brassinosteroid, and in particular to a germination growth accelerator, a cold resistance enhancer, and an accelerator for growing, thickening or maturing fruits, roots, stems or bulbs.

The present third invention relates to an epoxycyclohexane derivative represented by general formula (3):

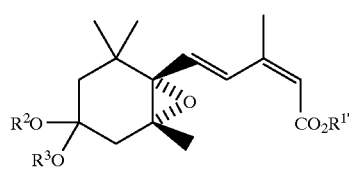

(3)

wherein $R^{1'}$ is a $C_2$–$C_6$ alkyl group or $C_3$–$C_6$ cycloalkyl group, and $R^2$ and $R^3$ are independently $C_1$–$C_6$ alkyl groups or are combined to form a $C_2$–$C_3$ polymethylene group which may be substituted with a $C_1$–$C_6$ alkyl group.

In general formula (1), the $C_1$–$C_6$ alkyl group represented by $R^1$ includes a methyl group, ethyl group, propyl group, isopropyl group, butyl group, isobutyl group, s-butyl group, t-butyl group, pentyl group, isopentyl group, hexyl group, s-hexyl group etc. Among these, $C_2$–$C_4$ groups, particularly propyl and isopropyl groups, are preferred for physiological actions.

In general formula (3), the $C_2$–$C_6$ alkyl group represented by $R^{1'}$ includes an ethyl group, propyl group, isopropyl group, butyl group, isobutyl group, s-butyl group, t-butyl group, pentyl group, isopentyl group, hexyl group, s-hexyl group etc. Among these, propyl and isopropyl groups are particularly preferred for stronger physiological actions.

In general formulae (1) and (3), the $C_3$–$C_6$ cycloalkyl group represented by $R^1$ and $R^{1'}$ includes a cyclopropyl group, cyclobutyl group, cyclopentyl group and cyclohexyl group.

In general formulae (1) and (3), the $C_1$–$C_6$ alkyl group represented by $R^2$ and $R^3$ is preferably a straight-chain $C_1$–$C_4$ alkyl group and includes a methyl group, ethyl group, propyl group and butyl group. The $C_2$–$C_3$ polymethylene group which may be substituted with a $C_1$–$C_6$ alkyl group includes an ethylene group, propylene group etc. Among these, an ethylene group is preferred for strong activity and easy synthesis. A substituent group optionally present in said polymethylene group includes the above-described $C_1$–$C_6$ alkyl group.

The brassinosteroids used in the present second invention include brassinolide and its analogues ("Shokubutsu No Kagaku Chosetsu" (Chemical Regulation of Plant), 22[1], 10–17 (1987); "Yukagaku" (Oil Chemistry), 39[4], 227–235 (1990)). The analogues include compounds developed by some of the present inventors, which are represented by general formula (2):

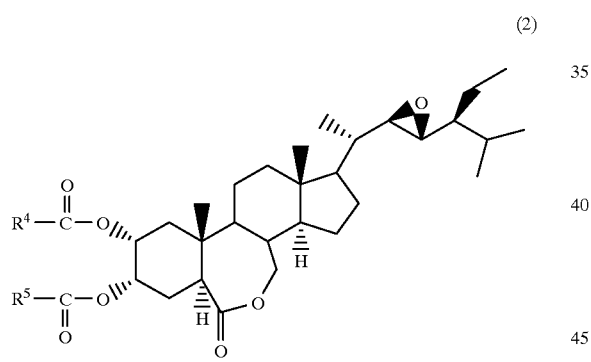

(2)

wherein $R^4$ and $R^5$ are $C_1$–$C_6$ lower alkyl groups ("Shokubutsu No Kagaku Chosetsu", 29[1], 23–30 (1994); Japanese Patent LOP Publication No. 125,396/1989).

The $C_1$–$C_6$ alkyl groups represented by $R^4$ and $R_5$ in general formula (2) are preferably $C_1$–$C_4$ straight-chain alkyl groups and include a methyl group, ethyl group, propyl group and butyl group. In particular, the ethyl group and propyl group are preferable for high activity.

The epoxycyclohexane derivatives represented by general formula (1) or (3) are produced generally as follows:

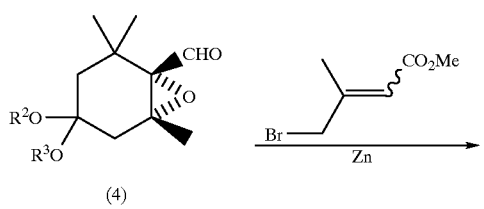

(4)

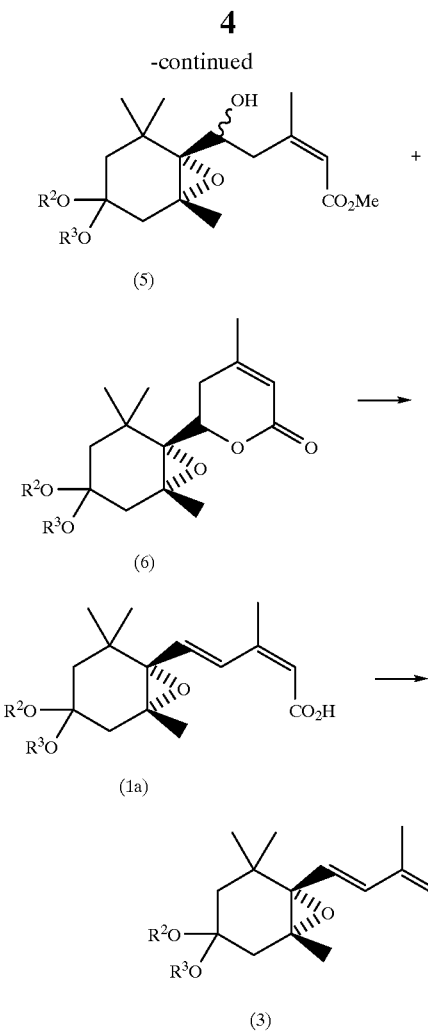

wherein $R^{1'}$, $R^2$ and $R^3$ have the same meanings as defined above.

Epoxycyclohexanecarbaldehyde (4) as the starting material can be synthesized by a method described in a literature (Helv. Chim. Acta, 71, 931 (1988)). The conversion of compound (4) into the carboxylic acid of formula (1a) can be effected by the method described in Japanese Patent LOP Publication No. 184,966/1991. The present compounds represented by formula (3) can be obtained by esterifying the carboxylic acid of formula (1a), e.g. in reaction with a corresponding alcohol in the presence of a condensation agent such as carbodiimide. Japanese Patent LOP Publication No. 184,966/1991 describes that compound (1b) of formula (1) wherein $R^1$ is a methyl group can be synthesized by allowing diazomethane to act on carboxylic acid (1a). However, this prior method is limited to synthesis of methyl ester and cannot be applied to synthesis of other esters.

The compounds of formula (2) used in the present second invention are obtained generally as follows:

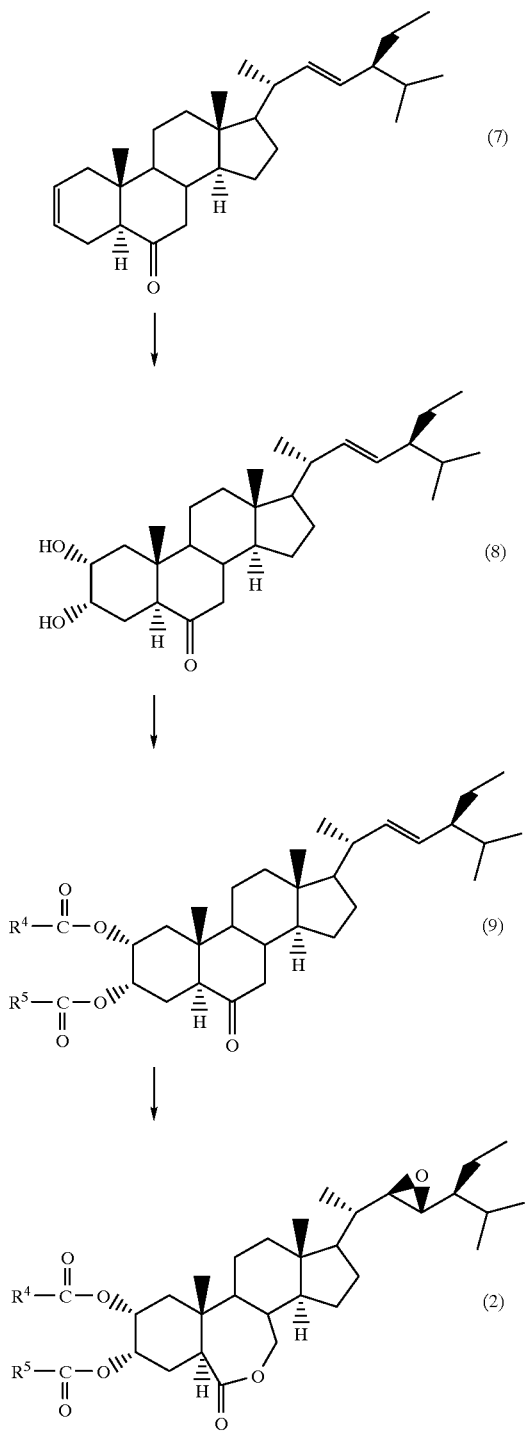

wherein R⁴ and R⁵ have the same meanings as defined above.

When (22E, 24S)-24-ethyl-5α-cholesta-2, 22-diene-6-one (7) (K. Mori, Agric. Biol. Chem., 44(5), 1211 (1980)) is subjected to catalytic hydroxylation with a catalytic amount of osmium tetraoxide in an inert gas such as nitrogen, argon etc. in the presence of t-butyl hydroperoxide or N-methylmorpholine-N-oxide, its dihydroxylation at the 2α- and 3α-positions proceeds selectively by regulating the amounts of the reactants, and 2 α, 3α-dihydroxy derivative (8) can be obtained in high yield. This dihydroxy derivative (8) is dissolved in pyridine containing 4-dimethylaminopyridine and reacted with a corresponding carboxylic anhydride (e.g. propionic anhydride, butyric anhydride, etc.) to give compound (9). Then, compound (9) is dissolved in a chlorinated organic solvent stable to oxidation and oxidized with organic peroxide, e.g. perbenzoic acid, m-monochloroperbenzoic acid, m-monobromoperbenzoic acid, monoperphthalic acid, trifluoroperacetic acid or their sodium or potassium salts tQ give the compound of formula (2).

As the plant growth regulator according to the present first invention, said epoxycyclohexane derivative can be mixed with conventional carriers, diluent etc. for application to plants or plant seeds in the form of e.g. liquid, powder, emulsion, wettable powder, granules etc. Conventional plant growth regulators, herbicides, fungicides and bactericides, insecticides and acaricides etc. can also be incorporated into it for use. Auxiliary agents such as spreader and stickers, emulsifier, wetting agent, dispersant, fixing agent, disintegrator etc. may further be added. These carriers, diluent, auxiliary agents etc. are preferably selected to optimize the regulatory action on plant growth.

The amount of the plant growth regulator according to the first invention varies depending on the application method and desired action. For application by spraying, for example, its concentration is preferably 1000 to 1 ppm, more preferably 100 to 5 ppm. For application by immersion of seeds etc., its concentration is preferably 1 to 0.001 ppm, more preferably 0.1 to 0.01 ppm.

As the plant growth regulator according to the present second invention, said epoxycyclohexane derivative and brassinosteroid can be mixed with conventional carriers, diluent etc. for application to plants or plant seeds in the form of e.g. liquid, powder, emulsion, wettable powder, granules etc. Conventional other plant growth regulators or herbicides, fungicides and bactericides, insecticides and acaricides etc. can also be incorporated into it for use. Auxiliary agents such as spreader and stickers, emulsifier, wetting agent, dispersant, fixing agent and disintegrator may further be added. These carriers, diluent, auxiliary agents etc. are preferably selected to optimize the regulatory action on plant growth.

The amount and mixing ratio of the epoxycyclohexane derivative and the brassinosteroid in the plant growth regulator according to the present second invention vary depending on the application method and desired action. For application by spraying, for example, it is preferable to mix the epoxycyclohexane derivative in the range of 100 to 0.1 ppm with the brassinosteroid in the range of 0.1 to 0.001 ppm.

The plants to which the plant growth regulators of the present first and second inventions are applied include, but are not limited to, vegetables such as spinach, Chinese cabbage, cucumber, eggplant, beefsteak plant, cabbage, garland chrysanthemum, leek and onion, root vegetables such as Japanese white radish, sweet potato, beet and potato, cereals such as rice, wheat and corn, beans such as soybean, adzuki bean and peanut, industrial crop, such as sugar cane and hemp, fruits such as grape, tangerine, persimmon, apple, tomato, melon, pear, strawberry, peach, banana, pineapple and coffee, ornamental plants such as rubber tree, phoenix and benjamin bush, and flowers such as chrysanthemum, carnation, rose, bellflower, lily and tulip.

BEST MODE FOR CARRYING OUT THE INVENTION

Hereinafter, the present invention is described in detail by reference to Examples and Test Examples, which however are not intended to limit the present invention.

EXAMPLE 1

Synthesis of (3b)

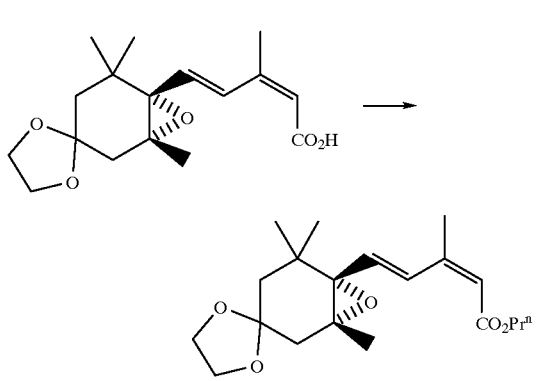

To 308 mg (1.00 mmol) of 4,4-ethylenedioxy-1-[4-(hydroxycarbonyl)-3-methyl-1,3-butadiene-1-yl]-1,2-oxo-2,6,6-trimethylcyclohexane (1a) (product obtained in the same manner as in Example 2 in Japanese Patent LOP Publication No. 184,966/1991) and 180 mg (224 μL, 3.00 mmol) of propyl alcohol in dry dichloromethane (1.5 mL) was added 98 mg (0.80 mmol) of p-dimethylaminopyridine (DMAP), and an argon gas was bubbled into the mixture under cooling on ice, and it was sealed in an argon atmosphere with stirring under cooling on ice, 227 mg (1.10 mmol) of dicyclohexyl carbodiimide in dichloromethane (10 mL) was added to it over a period of 5 minutes, and the mixture was stirred for 15 minutes under cooling on ice and then for 3 hours at room temperature. 10 mL diethyl ether was further added to the reaction solution in which a large amount of white precipitates had occurred, and the precipitates were removed by filtration. Diethyl ether was further added, and it was washed with an aqueous 2M hydrochloric acid/saturated sodium chloride solution, then with an aqueous saturated and hydrogen carbonate solution, and with an aqueous saturated sodium chloride solution. Then, the diethyl ether layer was separated and dried over anhydrous sodium sulfate. The solvent was distilled off, and the resulting crude oil, 385 mg, was purified by silica gel column chromatography (16 g of Wako Gel C-200™; hexane:ethyl acetate=4:1) to give 296 mg of 4,4-ethylenedioxy-1-[4-(propoxycarbonyl)-3-methyl-1,3-butadiene-1-yl]-1,2-oxo-2,6,6-trimethylcyclohexane (3b) as colorless oily matter (yield: 84 %).

$^1$H-NMR (CDCl$_3$) δ(ppm): 0.96 (3H, t, J=7.4), 1.00 (3H, s), 1.22 (3H, s), 1.25 (3H, s), 1.34 (1H, dd, J=2.1, 13.6), 1.68 (2H, dd, J=6.7, 7.4), 1.74 (1H, d, J=13.6), 2.01 (3H, d, J=1.3), 2.04 (1H, dd, J=2.1, 15.7), 2.28 (1H, d, J=15.7), 3.81–3.97 (4H, m), 4.07 (2H, d, J=6.7), 5.71 (1H, brs), 6.27 (1H, dd, J=0.6, 16.1), 7.62 (1H, dd, J=0.7, 16.1).

LRMS m/z: 350 (M$^+$), 291 (M$^+$—C$_3$H$_7$O), 264 (M$^+$—C$_4$H$_6$O$_2$).

HRMS m/z: Theoretical (as C$_{20}$H$_{30}$O$_5$) 350.2092; Found 350.2103.

[α]$_D^{20}$=10.22 (c 1.8, CHCl$_3$).

EXAMPLE 2

Synthesis of (3a)

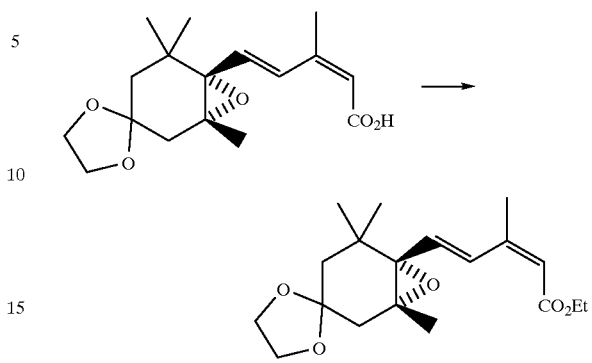

The same procedure as in Example 1 was repeated except that 138 mg (3.00 mmol) of ethyl alcohol was used in place of propyl alcohol, to give 264 mg of 4,4-ethylenedioxy-1-[4-(ethoxycarbonyl)-3-methyl-1,3-butadiene-1-yl-]-1,2-oxo-2,6,6-trimethylcyclohexane (3a) (1a) (yield: 78.5%).

$^1$H-NMR (CDCl$_3$) δ(ppm): 1.00 (3H, s), 1.22 (3H, s), 1.25 (3H, s), 1.38 (3H, t, J=7.1), 1.34 (1H, dd, J=2.1, 13.7), 1.75 (1H, d, J=13.7), 2.01 (3H, d, J=1.3), 2.05 (1H, dd, J=2.1, 15.7), 2.28 (1H, d, J=15.7), 3.82–3.96 (4H, m), 4.17 (2H, q, J=7.1), 5.70 (1H, brs), 6.27 (1H, dd, J=0.6, 16.0), 7.63 (1H, dd, J=0.8, 16.0).

LRMS m/z: 336 (M$^+$).

HRMS m/z: Theoretical (as C$_{19}$H$_{28}$O$_5$) 336.1935; Found 336.1913.

EXAMPLE 3

Synthesis of (3c)

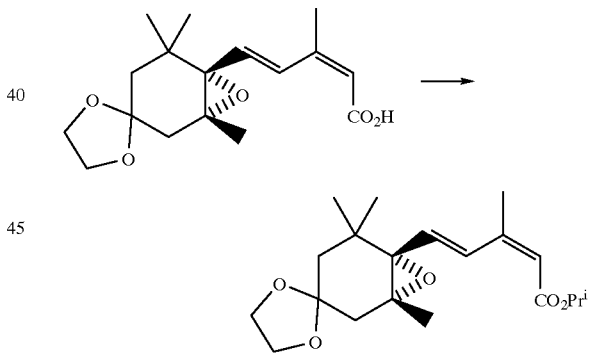

The same procedure as in Example 1 was repeated except that 180 mg (230 μL) of isopropyl alcohol was used in place of propyl alcohol, to give 282 mg of 4,4-ethylenedioxy-1-[4-(isopropoxycarbonyl) -3-methyl-1,3-butadiene-1-yl]-1,2-oxo-2,6,6-trimethylcyclohexane (3c) (yield: 18%).

$^1$H-NMR (CDCl$_3$) δ(ppm): 1.00 (3H, s), 1.22 (3H, s), 1.25 (3H, s), 1.26 (6H, d, J=6.3), 1.34 (1H, dd, J=2.1, 13.7), 1.74 (1H, d, J=13.7), 2.00 (3H, d, J=1.3), 2.04 (1H, dd, J=2.1, 15.8), 2.28 (1H, d, J=15.8), 3.81–3.94 (4H, m), 5.06 (1H, sept, J=6.3), 5.68 (1H, brs), 6.26 (1H, dd, J=0.6, 16.1), 7.61 (1H, dd, J=0.7, 16.1).

LRMS m/z: 350 (M$^+$), 291 (M$^+$—C$_3$H$_7$O), 264 (M$^+$—C$_4$H$_6$O$_2$).

HRMS m/z: Theoretical (as C$_{20}$H$_{30}$O$_5$) 350.2091; Found 350.2087.

[α]$_D^{20}$=13.00 (c 1.8, CHCl$_3$).

EXAMPLE 4
Synthesis of (3d)

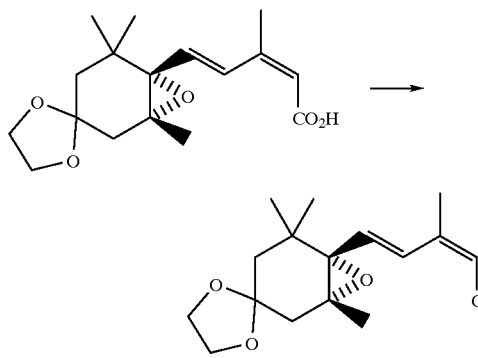

The same procedure as in Example 1 was repeated except that 227 mg (3.00 mmol) of butyl alcohol was used in place of propyl alcohol, to give 306 mg of 4,4-ethylenedioxy-1-[4-(butoxycarbonyl)-3-methyl-1,3-butadiene-1-yl]-1,2-oxo-2,6,6-trimethylcyclohexane (3d) (yield: 84%).

$^1$H-NMR (CDCl$_3$) δ(ppm): 0.94 (3H, t, J=7.4), 1.00 (3H, s), 1.22 (3H, s), 1.25 (3H, s), 1.34 (1H, dd, J=2.1, 13.7), 1.40 (2H, tq, J=7.4, 7.4), 1.64 (2H, tt, J=6.7, 7.4), 1.74 (1H, d, J=13.7), 2.01 (3H, d, J=1.2), 2.04 (1H, dd, J=2.1, 15.7), 2.28 (1H, d, J=15.7), 3.82–3.96 (4H, m), 4.12 (2H, t, J=6.7), 5.70 (1H, brs), 6.27 (1H, dd, J=0.5, 16.0), 7.63 (1H, dd, J=0.7, 16.0).

LRMS m/z: 364 (M$^+$).

HRMS m/z: Theoretical (as C$_{21}$H$_{32}$O$_5$) 364.2247; Found 364.2253.

EXAMPLE 5
Synthesis of (3e)

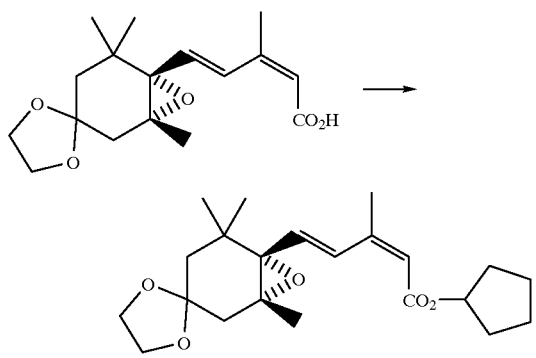

The same procedure as in Example 1 was repeated except that 258 mg (3.00 mmol) of cyclopentyl alcohol was used in place of propyl alcohol, to give 312 mg of 4,4-ethylenedioxy-1-[4-(cyclopentyloxycarbonyl)-3-methyl-1,3-butadiene-1-yl]-1,2-oxo-2,6,6-trimethylcyclohexane (3e) (yield: 83%).

$^1$H-NMR (CDCl$_3$) δ(ppm): 0.96 (3H, s), 1.21 (3H, s), 1.25 (3H, s), 1.34 (1H, dd, J=2.1, 13.7), 1.55–1.63 (m), 1.68–1.79 (m), 1.74 (1H, d, J=13.7), 1.81–1.93 (m), 2.00 (3H, d, J=1.2), 2.04 (1H, dd, J=2.1, 15.7), 2.27 (1H, d, J=15.7), 3.82–3.96 (4H, m), 5.22 (1H, m), 5.67 (1H, brs), 6.26 (1H, dd, J=0.6, 16.0), 7.60 (1H, dd, J=0.6, 16.0).

LRMS m/z: 376 (M$^+$).

HRMS m/z: Theoretical (as C$_{22}$H$_{32}$O$_5$) 376.2247; Found 376.2226.

Synthetic Example 1
Synthesis of (2a)

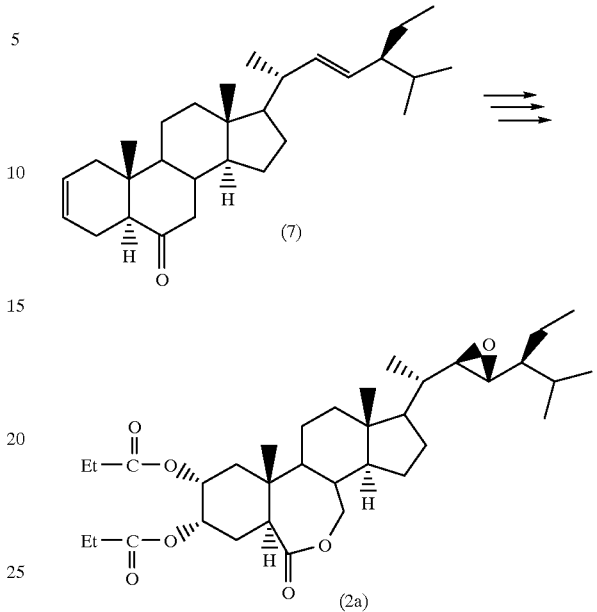

The same procedure as described in Japanese Patent LOP Publication No. 125,396/1989 was carried out to give (22R, 23R, 24S)-2α,3α-dipropionyloxy-22,23-epoxy-B-homo-7-oxa-5α-stigmastane-6-one (2a) as needle crystal.

m.p.: 147–148° C. (from methanol)

$^1$H-NMR (CDCl$_3$) δ(ppm): 0.72 (3H, s), 1.10 (3H, s), 1.18 (3H, s), 2.73 (1H, dd), 3.00 (1H, dd), 4.10 (2H, m), 4.89 (1H, m), 5.38 (1H, m).

FD-MS m/z: 589 (M$^+$+1).

Synthetic Example 2
Synthesis of (2b)

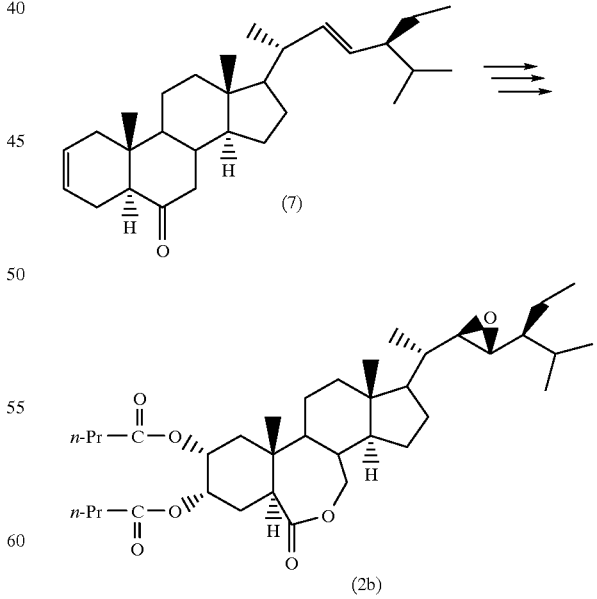

The same procedure as described in Japanese Patent LOP Publication No. 125,396/1989 was carried out to give (22R, 23R, 24S)-2 α,3α-dibutyroyloxy-22,23-epoxy-B-homo-7-oxa-5α-stigmastane-6-one (2b).

State: amorphous.
$^1$H-NMR (CDCl$_3$) δ(ppm): 0.67 (3H, s), 0.99 (3H, s), 2.70 (1H, dd), 3.00 (1H, dd), 4.10 (2H, m), 4.86 (1H, m), 5.36 (1H, m).
FD-MS m/z: 617 (M$^+$+1).

Test Example 1
Evaluation of Transpiration Suppressing and Growth Promoting Action Mangbean seeds were planted in vermiculite and grown at 22° C. under continuous fluorescent-lamp lighting. On the date when their primordial leaves were developed (epicotyl length, 2 cm), their primordial leaves and epicotyls were sprayed uniformly with a treatment solution of each test compound. The treatment solution was prepared by dissolving each test compound in a small amount of Etoll™ and diluting it with water at a predetermined concentration.

Seven seedling per group were grown in the same manner as above in a vessel with 100 mL water containing a liquid fertilizer (Hyponex™).

Four days after the treatment, i.e. when the elongation growth of their epicotyl was completely finished, the transpiration in each treatment group (reduction in the amount of water in each vessel) and their average weight were determined and expressed in percentage based on that of the non-treatment group (%). The results are shown in Tables 1 and 2.

Table 1. Results of Suppression of Transpiration

| Compound | Transpiration (%)* Concentration (ppm) | |
| --- | --- | --- |
| | 10 | 1 |
| Compound (1a) | 84.6 | 88.6 |
| Compound (1b) | 81.4 | 83.2 |
| Compound (3a) | 78.6 | 84.4 |
| Compound (3b) | 79.6 | 82.8 |
| Compound (3c) | 76.3 | 79.5 |
| Compound (3d) | 88.6 | 90.9 |
| Compound (3e) | 87.2 | 92.7 |
| Natural type abscisic acid | 82.7 | 87.6 |
| Non-treatment | 100.0 | (4.92 ml/plant/4 days) |

Table 2. Results of Growth Promotion

| Compound | Average weight of Plant (%)* Concentration (ppm) | |
| --- | --- | --- |
| | 10 | 1 |
| Compound (1a) | 110.4 | 107.7 |
| Compound (1b) | 114.9 | 109.3 |
| Compound (3a) | 113.0 | 111.0 |
| Compound (3b) | 115.2 | 112.6 |
| Compound (3c) | 116.5 | 113.8 |
| Compound (3d) | 106.1 | 103.0 |
| Compound (3e) | 105.3 | 101.2 |
| Natural type abscisic acid | 109.6 | 105.2 |
| Non-treatment | 100.0 | (564 mg/plant) |

*Percentage relative to the non-treatment group as 100%.

As is evident from the above results, the compounds of the present invention indicated an activity which was almost equivalent to or higher than that of natural type abscisic acid. In particular, compounds (3b) and (3c) indicated a 10-fold or more activity than that of natural type abscisic acid.

Test Example 2
Evaluation of Seed Germination and Growth Promoting Action (1)

Unhulled rice seeds (variety: Nihon Bare) were immersed in water at 15° C. for 1 day and then immersed in an aqueous solution of each test compound at a predetermined concentration for 24 hours. Fifteen seeds were planted in each pot (diameter: 10 cm) packed with vermiculite and grown in a room under artificial conditions at a temperature of 20 to 21° C. under continuous lighting at 15,000 lux. Meanwhile, a liquid fertilizer (Hyponex™) was given.

At the 4-leaf stage, 10 well-grown seedlings were picked up from each pot (2 pots in each group, 20 seedlings in total), and the average weight of seedlings including roots was determined and expressed in percentage based on that of the non-treatment group. The results are shown in Table 3.

TABLE 3

Results of Promotion of Seed Germination and Growth

| Compound | Average Weight of Seedlings (%)* Concentration (ppm) | |
| --- | --- | --- |
| | 0.1 | 0.01 |
| Compound (1a) | 103.9 | 106.4 |
| Compound (1b) | 102.7 | 108.8 |
| Compound (3a) | 104.5 | 111.2 |
| Compound (3b) | 108.2 | 114.9 |
| Compound (3c) | 110.2 | 113.4 |
| Compound (3d) | 102.8 | 105.3 |
| Compound (3e) | 99.1 | 102.0 |
| Natural type abscisic acid | 108.5 | 105.9 |
| Non-treatment | 100.0 | (171 mg/seedling) |

*Percentage relative to the non-treatment group as 100%.

As is evident from the above results, the compounds of the present invention indicated an activity which was almost equivalent to or higher than that of natural type abscisic acid.

Test Example 3
Evaluation of Seed Germination and Growth Promoting Action (2)

Carrot seeds (variety: Koyo No. 2) were immersed instantaneously in a solution of a test compound in ethanol/water (50:50) at a predetermined concentration. Immediately after the treatment, the treated seeds were air-dried, and on the next day, they were planted and cultivated in a vinyl house at a temperature of 13° C. or more at night.

Sixty days after planting, the average weight of their roots was determined and expressed in percentage based on that of the non-treatment group. The results are shown in Table 4.

TABLE 4

Results of Promotion of Seed Germination and Growth

| Compound | Average Weight of Roots (%)* Concentration 0.1 ppm |
| --- | --- |
| Compound (1a) | 110.7 |
| Compound (1b) | 115.0 |
| Compound (3a) | 115.9 |
| Compound (3b) | 117.2 |
| Compound (3c) | 118.8 |
| Compound (3d) | 113.1 |
| Compound (3e) | 108.0 |
| Natural type abscisic acid | 111.5 |
| Non-treatment | 100.0 |

*Percentage relative to the non-treatment group as 100%

As is evident from the above results, the compounds of the present invention exhibited an activity which was almost equivalent to or higher than that of natural type abscisic acid.

Test Example 4
Evaluation of Fruit Maturation promoting Action

A grape variety, Kyoho, grown outdoors for 20 years was treated with the compound (3c) of the present invention or natural type abscisic acid. In this treatment, each test compound was dissolved in 80% ethanol at a predetermined concentration and 5 ml solution was sprayed on each cluster at the timing of beginning to color. Seventeen days after spraying, the fruits were harvested and examined for their qualities. The results are shown in Table 5.

TABLE 5

Results of Promotion of Fruit Maturation

| Compound | Concentration (ppm) | Coloration Degree | Sugar Degree (Brix %) | Acidity (%) |
| --- | --- | --- | --- | --- |
| Compound (3c) | 50 | 5.7 | 15.7 | 0.68 |
| Natural type abscisic acid | 300 | 5.8 | 15.8 | 0.66 |
|  | 50 | 5.3 | 15.4 | 0.74 |
| Non-treatment |  | 4.6 | 14.7 | 0.80 |

*Percentage relative to the non-treatment group as 100%

As is evident from the above results, the activity of 50 ppm compound (3c) according to the present invention was comparable to that of 300 ppm natural type abscisic acid, indicating that the former compound had about 5-times activity as high as that of the latter.

Test Example 5
Evaluation of Root Thickening and Growth Promoting Action

Radishes (early var. Akamaru-commet) were cultivated in a field and a test compound was sprayed on it when their root thickening began. The spray liquid was prepared as follows: Ninety-five parts by weight of a solvent consisting of 60 parts of xylene, 20 parts of isophorone and 20 parts of a surfactant were mixed with 5 parts by weight of a test compound to give an emulsion preparation. It was diluted with water at a predetermined concentration and then sprayed in an amount of 100 liters/1,000 m².

Fifteen days after spraying, the average weight of their roots in each group was determined and expressed in percentage based on that of the non-treatment group. The results are shown in Table 6.

TABLE 6

Results of Root Thickening and Growth Promotion

| Compound | Average Weight of Roots (%)* Concentration 5 ppm |
| --- | --- |
| Compound (1a) | 109.8 |
| Compound (1b) | 112.3 |
| Compound (3a) | 111.2 |
| Compound (3b) | 114.0 |
| Compound (3c) | 115.4 |
| Compound (3d) | 110.6 |
| Compound (3e) | 109.0 |
| Natural type abscisic acid | 108.5 |
| Non-treatment | 100.0 |

*Percentage relative to the non-treatment group as 100%

As is evident from the above results, the compounds of the present invention exhibited an activity which was almost equivalent to or higher than that of natural type abscisic acid.

Test Example 6
Evaluation of Cold Resistance Enhancing Action

Each test compound was sprayed on a Benjamin plant with 150 to 200 leaves, cultivated in a pot in a greenhouse. The spraying liquid was prepared as follows: Ninety-five parts by weight of a solvent consisting of 60 parts of xylene, 20 parts of isophorone and 20 parts of a surfactant were mixed with 5 parts by weight of a test compound to give an emulsion preparation. It was diluted with water at a predetermined concentration. The whole of leaves was sprayed and soaked uniformly with the test solution.

From the day after spraying (early November), the plant was placed at ambient temperatures in an open field. The percentage of fallen leaves after 25 days was determined. The results are shown in Table 7.

TABLE 7

Results of Prevention of Fallen Leaves Due to Cold Damage

| Compound | Percentage of Fallen Leave (%) Concentration 10 ppm |
| --- | --- |
| Compound (1a) | 30.4 |
| Compound (1b) | 25.3 |
| Compound (3a) | 20.0 |
| Compound (3b) | 18.8 |
| Compound (3c) | 16.5 |
| Compound (3d) | 27.0 |
| Compound (3e) | 38.2 |
| Natural type abscisic acid | 37.1 |
| Non-treatment | 91.3 |

As is evident from the above results, the compounds of the present invention exhibited the activity of preventing leaves from falling due to cold damage, which was almost equivalent to or higher than that of natural type abscisic acid.

Test Example 7
Evaluation of Seed Germination and Growth Promoting Action (Combination with Brassinosteroid) (1)

Unhulled rice seeds (variety: Nihon Bare) were immersed in water at 15° C. for 1 day and then immersed in an aqueous solution of each test compound at a predetermined concentration [treatment with a single compound: 0.01 ppm compound; and treatment with a mixture: 0.01 ppm compound (1a, 1b, 3a to 3e), or 0.01 ppm natural type abscisic acid, plus 0.01 ppm compound (2a)] for 24 hours. Fifteen seeds were planted in each pot (diameter: 10 cm) packed with vermiculite and grown in a room under artificial conditions at a temperature of 20 to 21° C. under continuous lighting at 15,000 lux. Meanwhile, a liquid fertilizer (Hyponex™) was given.

At the 4-leaf stage, 10 well-grown seedlings were picked up from each pot (2 pots in each group, 20 seedlings in total), and the average weight of seedlings including roots was determined and expressed in percentage based on that of the non-treatment group. The results are shown in Table 8.

TABLE 8

Results of Promotion of Seed Germination and Growth

| | Average Weight of Seedlings (%)* treatment with | |
| --- | --- | --- |
| Compound | a single compound | a mixture |
| Compound (1a) | 106.4 | 119.3 |
| Compound (1b) | 108.8 | 118.1 |
| Compound (3a) | 111.2 | 120.4 |
| Compound (3b) | 114.9 | 126.6 |
| Compound (3c) | 113.4 | 128.0 |
| Compound (3d) | 105.3 | 115.7 |
| Compound (3e) | 102.0 | 107.0 |
| Compound (2a) | 108.6 | — |
| Natural type abscisic acid | 105.9 | 116.5 |
| Non-treatment | 100.0 | (171 mg/seedling) |

*Percentage relative to the non-treatment group as 100%.

As is evident from the above results, the treatment with a mixture showed a synergistic enhancing effect on germination and growth. In particular, the combination of compound (2a) with compound (3b) or (3c) showed a strong effect.

Test Example 8
Evaluation of Seed Germination and Growth Promoting Action (Combination with Brassinosteroid) (2)

Carrot seeds (variety: Koyo No. 2) were immersed instantaneously in a solution of a test compound in ethanol/water (50:50) at a predetermined concentration [treatment with a single compound: 0.1 ppm Compound (1a, 1b, 3a to 3e) or natural type abscisic acid or 0.01 ppm Compound (2a); and treatment with a mixture: 0.1 ppm Compound (1a, 1b, 3a to 3e), or 0.1 ppm natural type abscisic acid, plus 0.01 ppm Compound (2a)]. Immediately after the treatment, the treated seeds were air-dried, and on the next day, they were planted and cultivated in a vinyl house at a temperature of 13° C. or more at night.

Sixty days after planting, the average weight of their roots was determined and expressed in percentage based on that of the non-treatment group. The results are shown in Table 9.

TABLE 9

Results of Promotion of Seed Germination and Growth

| Compound | Average Weight of Roots (%)* treatment with | |
|---|---|---|
| | a single compound | a mixture |
| Compound (1a) | 110.7 | 127.0 |
| Compound (1b) | 115.0 | 128.1 |
| Compound (3a) | 115.9 | 131.4 |
| Compound (3b) | 117.2 | 138.5 |
| Compound (3c) | 118.8 | 135.1 |
| Compound (3d) | 113.1 | 125.6 |
| Compound (3e) | 108.0 | 120.0 |
| Compound (2a) | 109.0 | — |
| natural type abscisic acid | 111.5 | 125.9 |
| Non-treatment | 100.0 | |

*Percentage relative to the non-treatment group as 100%.

As is evident from the above results, the treatment with a mixture showed a synergistic effect on growth.

Test Example 9
Evaluation of Root Thickening and Growth Promoting Action (Combination with Brassinosteroid)

Radishes (early var. Akamaru-commet) were cultivated in a field and a test compound was sprayed on it when their root thickening began. The spray liquid was prepared as follows: Ninety-five parts by weight of a solvent consisting of 60 parts of xylene, 20 parts of isophorone and 20 parts of a surfactant were mixed with 5 parts by weight of a test compound to give an emulsion preparation. It was diluted with water at a predetermined concentration [treatment with a single compound: 5 ppm compound (1a, 1b, 3a to 3e) or natural type abscisic acid, or 0.01 ppm compound (2a); and treatment with a mixture: 5 ppm compound (1a, 1b, 3a to 3e), or 5 ppm natural type abscisic acid, plus 0.01 ppm compound (2a)] and then sprayed in an amount of 100 liters/1,000 m².

Fifteen days after spraying, the average weight of roots in each group was determined and expressed in percentage based on that of the non-treatment group. The results are shown in Table 10.

TABLE 10

Results of Root Thickening and Growth Promotion

| Compound | Average Weight of Roots (%)* treatment with | |
|---|---|---|
| | a single compound | a mixture |
| Compound (1a) | 109.8 | 120.2 |
| Compound (1b) | 112.3 | 124.7 |
| Compound (3a) | 111.2 | 125.0 |
| Compound (3b) | 114.0 | 128.4 |
| Compound (3c) | 115.4 | 127.6 |
| Compound (3d) | 110.6 | 119.2 |
| Compound (3e) | 109.0 | 116.5 |
| Compound (2a) | 107.4 | — |
| natural type abscisic acid | 108.5 | 118.1 |
| Non-treatment | 100.0 | |

*Percentage relative to the non-treatment group as 100%.

As is evident from the above results, the treatment with a mixture showed a synergistic effect on growth.

Test Example 10
Evaluation of Cold Resistance Enhancing Action (Combination with Brassinosteroid)

A test compound was sprayed on a Benjamin plant with 150 to 200 leaves, cultivated in a pot in a greenhouse. The spraying liquid was prepared as follows: Ninety-five parts by weight of a solvent consisting of 60 parts of xylene, 20 parts of isophorone and 20 parts of a surfactant were mixed with 5 parts by weight of a test compound to give an emulsion preparation. It was diluted with water at a predetermined concentration [treatment with a single compound: 10 ppm compound (1a, 1b, 3a to 3e) or natural type abscisic acid, or 0.01 ppm compound (2a), and treatment with a mixture: 10 ppm compound (1a, 1b, 3a to 3e), or 10 ppm natural type abscisic acid, plus 0.01 ppm compound (2a)]. The whole of leaves was sprayed and soaked uniformly with the test solution.

From the day after spraying (early November), the plant was placed at ambient temperatures in an open field. The percentage of fallen leaves after 25 days was determined. The results are shown in Table 11.

TABLE 11

Results of Prevention of Fallen Leaves Due to Cold Damage

| Compound | Percentage of Fallen Leave (%) treatment with | |
|---|---|---|
| | a single compound | a mixture |
| Compound (1a) | 30.4 | 22.4 |
| Compound (1b) | 25.3 | 18.0 |
| Compound (3a) | 20.0 | 17.1 |
| Compound (3b) | 18.8 | 13.7 |
| Compound (3c) | 16.5 | 11.8 |
| Compound (3d) | 27.0 | 25.9 |
| Compound (3e) | 38.2 | 26.0 |
| Compound (2a) | 28.6 | — |
| natural type abscisic acid | 37.1 | 20.8 |
| Non-treatment | 91.3 | |

As is evident from the above results, the treatment with a mixture showed a synergistic effect in preventing leaves from falling.

Industrial Applicability

The epoxycyclohexane derivatives of the present invention exhibit potent plant growth regulating actions equivalent to or higher than those of abscisic acid, such as plant growth promoting action, a germination growth promoting action, transpiration and wilting preventing action, cold resistance enhancing (low-temperature-damage preventing) action, and plant thickening and growth promoting action, and are useful as plant growth regulators such as a plant growth accelerator, a germination growth accelerator, a transpiration wilting inhibitor, a cold resistance enhancer, and an accelerator for growing, thickening or maturing fruits, roots, stems or bulbs. They are also useful as plant growth regulators such as a regulator for falling unmatured fruits, a bolting inhibitor, a preservative for cut flowers, a flowering inhibitor etc. which are known in the application of abscisic acid. Besides, they will be applicable to brewing for improvement in qualities and reduction in costs in brewing beer. The epoxycyclohexane derivatives of the present invention can be easily synthesized and thus supplied in large amounts as necessary.

The plant growth regulator of the present second invention, which comprises the epoxycyclohexane derivative and brassinosteroid as active ingredients, exerts synergistic actions on plant growth regulation, such as germination growth promoting action, cold resistance enhancing (low-temperature-damage preventing) action, and plant thickening and growth promoting action, and are useful as plant growth regulators such as a germination growth accelerator, a cold resistance enhancer, an accelerator for growing, thickening or maturing fruits, roots, stems or bulbs, a cutting-rooting accelerator, etc.

We claim:

1. A plant growth regulating composition comprising as an active ingredient an epoxycyclohexane derivative represented by general formula (1):

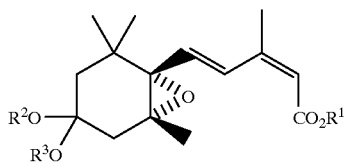

(1)

wherein $R^1$ is a hydrogen atom, a $C_1$–$C_6$ alkyl group or $C_3$–$C_6$ cycloalkyl group, and $R^2$ and $R^3$ are independently $C_1$–$C_6$ alkyl groups or are combined to form a $C_2$–$C_3$ polymethylene group which may be substituted with a $C_1$–$C_6$ alkyl group, and a brassinosteroid as active ingredients.

2. The plant growth regulating composition according to claim 1, wherein $R^1$ is a propyl or isopropyl group, and $R^2$ and $R^3$ are combined to form an ethylene group.

3. The plant growth regulating composition according to claim 1, wherein the brassinosteroid is a compound represented by general formula (2):

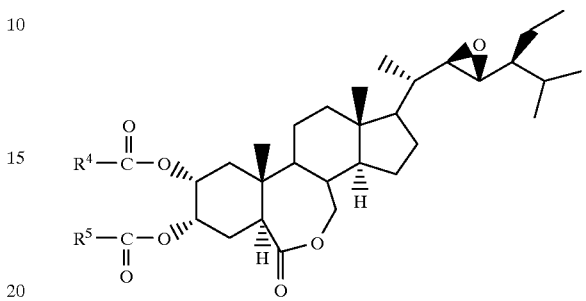

(2)

wherein $R^4$ and $R^5$ are independently $C_1$–$C_6$ alkyl groups.

4. The plant growth regulating composition according to claim 1, wherein the composition is a germination growth accelerator.

5. The plant growth regulating composition according to claim 1, wherein the composition is a cold resistance enhancer.

6. The plant growth regulating composition according to claim 1, wherein the composition is an accelerator for growing, thickening or maturing fruits, roots, stems or bulbs.

7. A method of regulating plant growth comprising applying the composition according to claim 1 onto a plant.

8. The method of claim 7, wherein the regulation is acceleration of germination growth.

9. The method of claim 7, wherein the regulation is inhibition of transpiration and wilting.

10. The method of claim 7, wherein the regulation is enhanced cold resistance.

11. The method of claim 7, wherein the regulation is acceleration of growing, thickening or maturing fruits, roots, stems or bulbs.

12. The method of claim 7, wherein the regulation is acceleration of plant growth.

* * * * *